United States Patent
Gulati

(10) Patent No.: US 7,322,135 B2
(45) Date of Patent: Jan. 29, 2008

(54) DEVICE FOR MEDICAL INSTRUMENT

(76) Inventor: Geeta Wagle Gulati, 2579 Hall Johnson Rd., Apt. 312, Grapevine, TX (US) 76051

(*) Notice: Subject to any disclaimer, the term of this patent is extended or adjusted under 35 U.S.C. 154(b) by 169 days.

(21) Appl. No.: 10/727,316

(22) Filed: Dec. 2, 2003

(65) Prior Publication Data

US 2004/0107610 A1 Jun. 10, 2004

Related U.S. Application Data

(60) Provisional application No. 60/430,287, filed on Dec. 2, 2002.

(51) Int. Cl.
G09F 3/10 (2006.01)
(52) U.S. Cl. .................... 40/316; 181/131
(58) Field of Classification Search ............ 40/316; 181/131
See application file for complete search history.

(56) References Cited

U.S. PATENT DOCUMENTS

| | | | |
|---|---|---|---|
| 1,282,511 A | 10/1918 | Williams et al. | |
| 2,819,824 A | 1/1958 | Ebert | |
| 3,885,742 A | 5/1975 | Menzel | |
| 4,092,002 A | 5/1978 | Grosse et al. | |
| 4,244,525 A * | 1/1981 | Manna | 239/289 |
| 4,454,877 A | 6/1984 | Miller et al. | |
| 4,497,124 A | 2/1985 | Olive | |
| 4,802,550 A | 2/1989 | Poore | |
| 5,172,683 A * | 12/1992 | West | 126/263.05 |
| D342,098 S | 12/1993 | Wolff | |
| D354,086 S | 1/1995 | Rashman | |
| D379,935 S | 6/1997 | Jornacion | |
| 5,663,533 A | 9/1997 | Judge | |
| D407,453 S | 3/1999 | Rashman | |
| D438,908 S * | 3/2001 | Najmi | D20/28 |
| 6,202,784 B1 | 3/2001 | Alatriste | |
| D453,193 S | 1/2002 | Isaacs et al. | |
| 2002/0066219 A1 | 6/2002 | Weidman et al. | |
| 2002/0157896 A1* | 10/2002 | Bates | 181/131 |
| 2003/0131398 A1* | 7/2003 | Haines | 2/312 |
| 2004/0046050 A1* | 3/2004 | Tai et al. | 239/289 |

FOREIGN PATENT DOCUMENTS

CH 690 545 A5 * 10/2000

* cited by examiner

Primary Examiner—Cassandra Davis
(74) Attorney, Agent, or Firm—Munsch Hardt Kopf & Harr, P.C.

(57) ABSTRACT

A device for a medical instrument comprises an information tag connector adapted to couple with the medical instrument, the information tag connector further adapted to removably couple with at least one accessory.

6 Claims, 4 Drawing Sheets

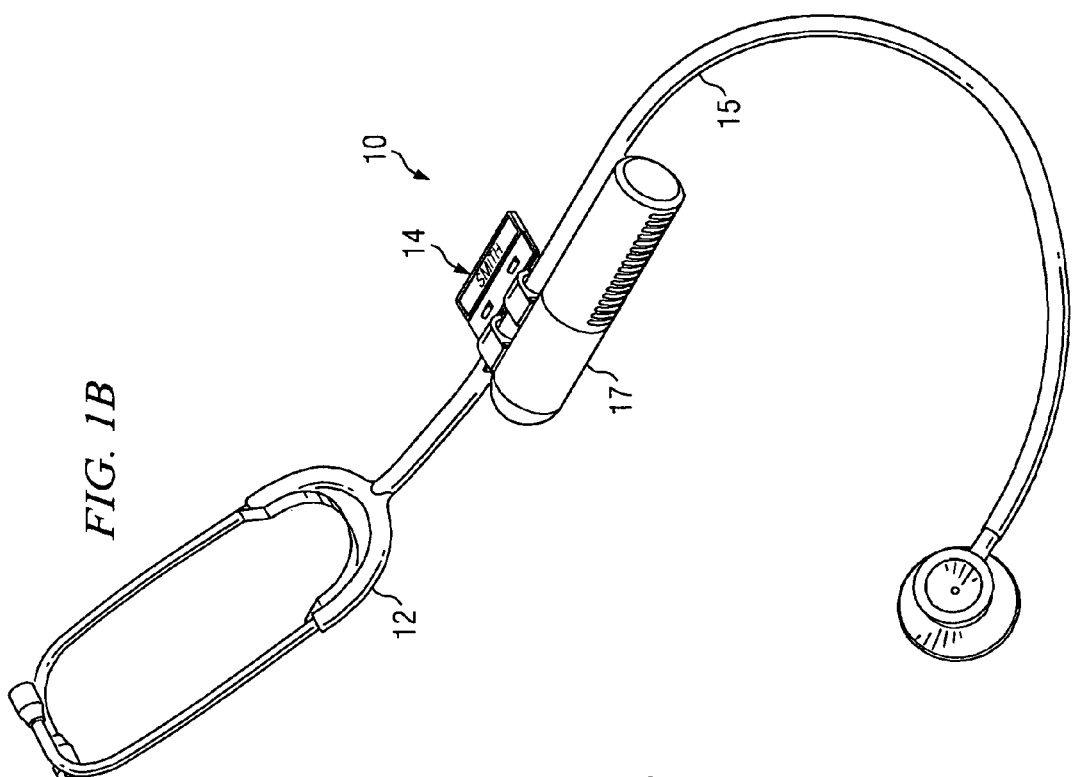
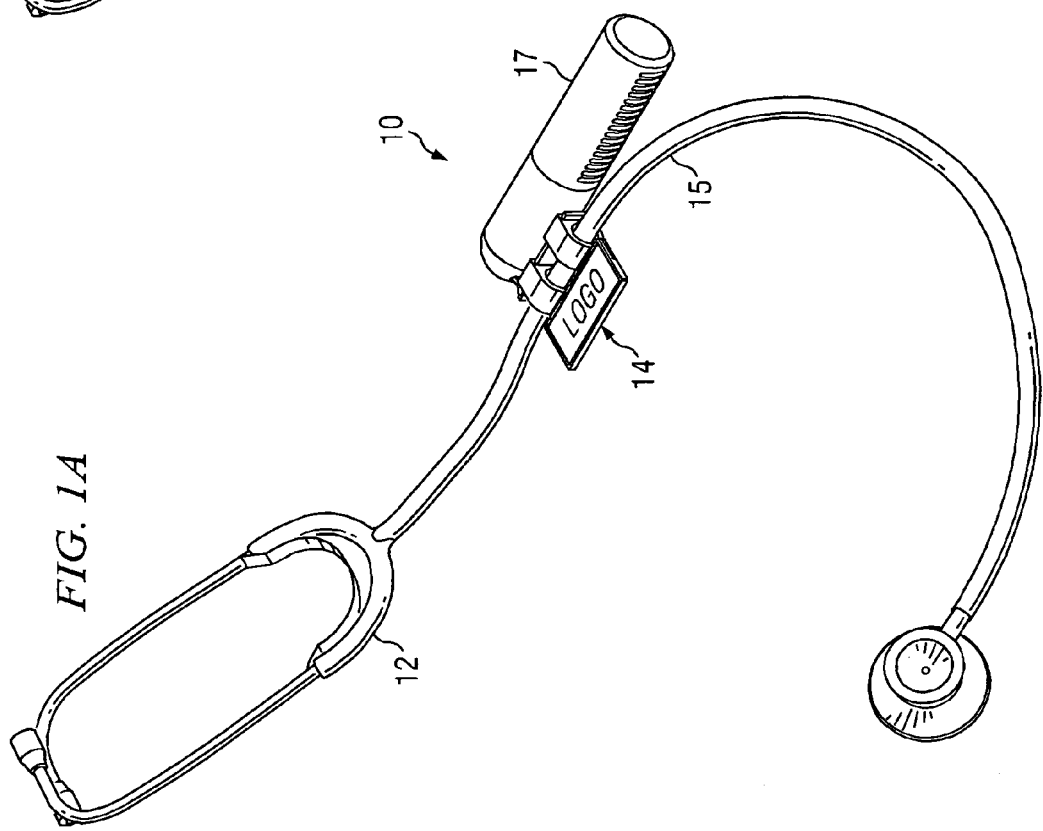

DEVICE FOR MEDICAL INSTRUMENT

RELATED APPLICATIONS

This patent application claims the benefit of U.S. Provisional Application No. 60/430,287, entitled, "Device for Medical Instrument," filed on Dec. 2, 2002, the disclosure of which is incorporated herein by reference.

TECHNICAL FIELD

The present invention relates generally to the field of medical instruments.

BACKGROUND

The most common way of disinfecting parts of a medical instrument, for example a stethoscope head and other parts of the stethoscope, is by wiping the instrument using a common disinfectant, such as standard isopropyl alcohol. Disinfecting of parts of a medical instrument, for example a stethoscope, should be performed after each use with a patient. However, the reality is that most health care workers do not perform this disinfection frequently enough and thus, increase the likelihood of acting as a carrier for harmful bacteria, viruses and fungi between patients. This could result in higher patient infection rates. Particularly in the hospital setting or other institutional medical setting, such as nursing homes, long term care facilities, and hemodialysis centers, failure to regularly disinfect a medical instrument could result in higher rates of nosocomial infections. Nosocomial infections can be severe, and even life threatening. The issue has become even more relevant with the emergence of several multi-drug resistant organisms that can cause severe infection in humans, such as methicillin resistant staphylococcal aureus (MRSA), Severe Acute Respiratory Syndrome (SARS) virus and vancomycin resistant enterococcus (VRE). In the case of MRSA, such bacteria are commonly discovered in the respiratory tract (nasal mucosa) and in the case of VRE, such bacteria are commonly discovered in the gastrointestinal tract of those individuals who are carriers, as well as on contaminated medical surfaces in the health care environment. These bacteria can cause severe disease in the susceptible patient.

It is believed that these bacteria can often be effectively made harmless on contaminated surfaces, such as stethoscope parts, by simple practice of standard disinfection guidelines. In the case of a medical instrument, such as a stethoscope, this involves the use of standard isopropyl alcohol or other disinfectant. Regular disinfection of the stethoscope should help reduce cross contamination between patients, and possibly impact the overall nosocomial infection rate. One of the main barriers to regular disinfection of the stethoscope parts is the convenience component of such an action.

SUMMARY

In accordance with an exemplary embodiment of the present invention, a device, for example an information tag connector, for use with an instrument, such as a medical instrument, for example a stethoscope, is provided. The information tag connector is adapted to be removably couplable with at least a portion of the instrument and is also adapted to be removably couplable with an accessory, for example a spray bottle, a calculator, a watch, a storage container, a writing instrument, or any other medical or non-medical accessory. The information tag connector when coupled to the medical instrument may be used to identify a user of the medical instrument, for example a health care worker. When a disinfectant spray bottle is coupled to the information tag connector, the information tag connector provides convenient access to a disinfectant for the user. The health care worker may thus carry a disinfectant with his stethoscope which makes it convenient for the worker to disinfect various parts of the stethoscope between patients. The disinfectant spray may also be used to disinfect other medical instruments or surfaces where contamination risk exists.

BRIEF DESCRIPTION OF THE DRAWINGS

For a more complete understanding of the present invention, the objects and advantages thereof, reference is now made to the following descriptions taken in connection with the accompanying drawings in which:

FIG. 1A is a perspective view illustrating a first surface of an exemplary information tag connector coupled to an exemplary instrument and an exemplary accessory;

FIG. 1B is a perspective view illustrating a back surface of the information tag connector coupled to the medical instrument and the accessory of FIG. 1A;

DETAILED DESCRIPTION OF THE DRAWINGS

Figure 2A:
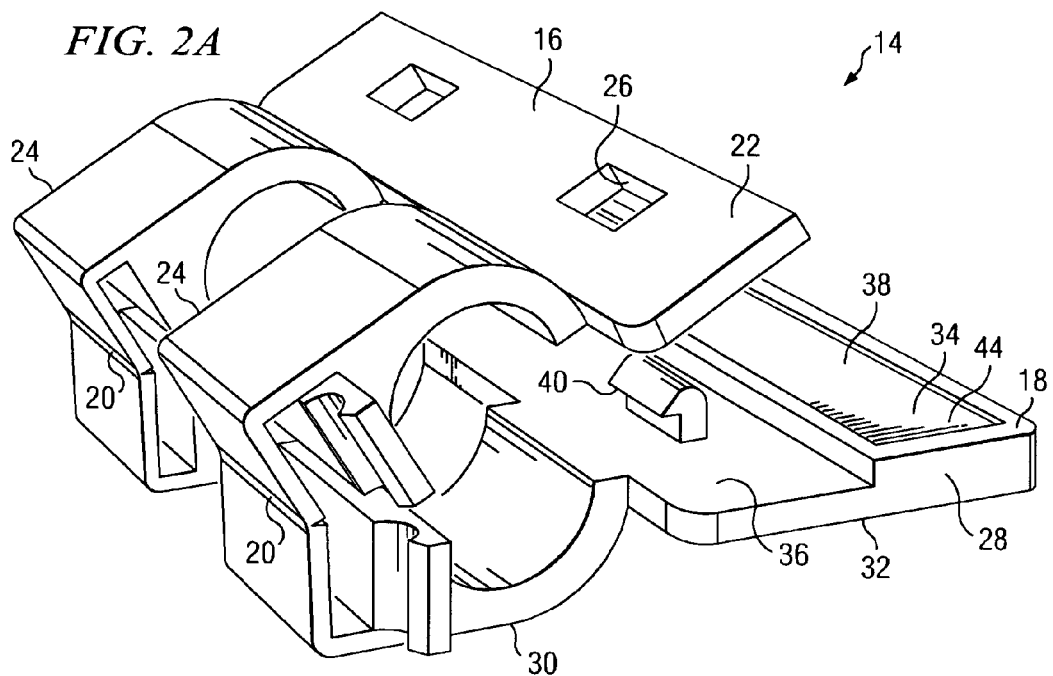
FIG. 2A is a perspective view of the information tag connector in an unlocked position.

The preferred embodiment of the present invention and its advantages are best understood by referring to FIGS. 1 through 3B of the drawings, like numerals being used for like and corresponding parts of the various drawings.

FIG. 1A is a perspective view illustrating an exemplary instrument disinfecting system 10. FIG. 1B is another perspective view illustrating system 10. System 10 comprises a device 14, for example an information tag connector, coupled to an instrument 12, such as a medical instrument, for example a stethoscope. For the sake of convenience, the illustrated embodiment of the present invention will be described herein with reference to a stethoscope, although the teachings of the present invention may be used with other types of instruments. For the sake of convenience, the illustrated embodiment of the present invention will be described herein with reference to an information tag connector, although the teachings of the present invention may be used with other types of devices. Connector 14 is coupled to a hose 15 of stethoscope 12. Preferably, connector 14 is removably coupled to stethoscope 12. If desired, connector 14 may be fixedly coupled to stethoscope 12 and/or may be part of stethoscope 12. In the illustrated embodiment, an accessory 17 is also coupled to connector 14. The accessory may be a spray bottle, a calculator, a watch, a storage container, a writing instrument, a portable light source, a ruler instrument, a voice recorder, or any other medical or non-medical accessory. Preferably, accessory 17 is removably coupled to connector 14. In an exemplary embodiment, system 10 comprises connector 14 and a disinfection spray bottle. In another exemplary embodiment, system 10 comprises connector 14 and a storage container.

Figure 2B:
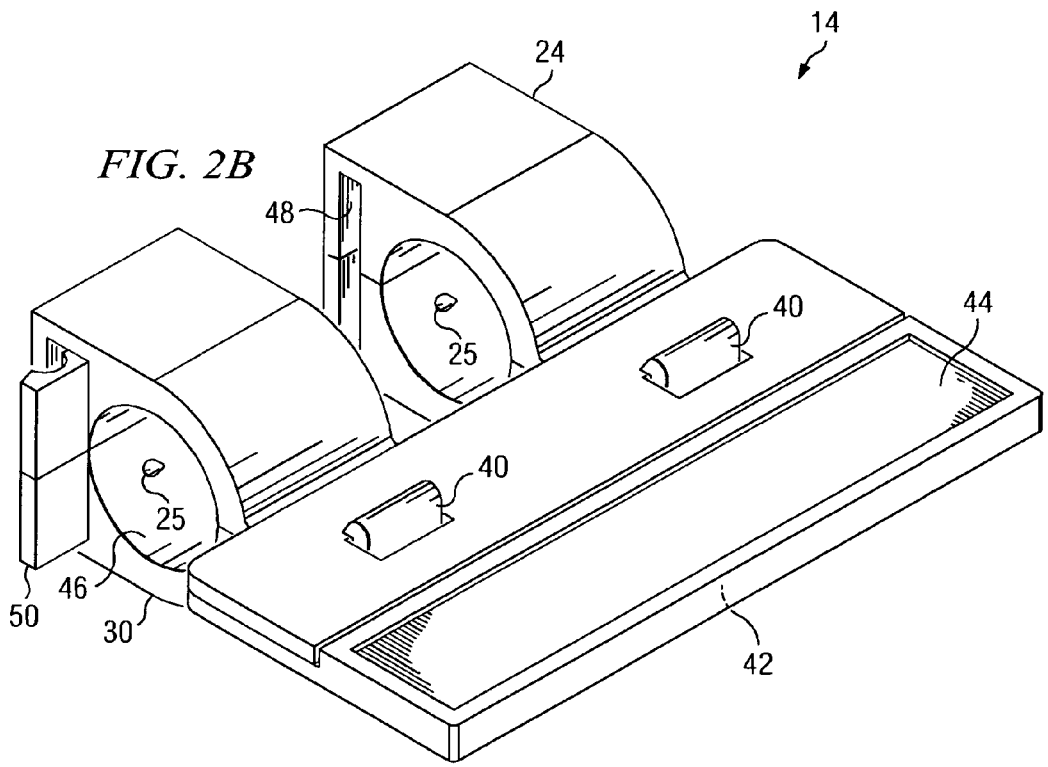
FIG. 2B is a perspective view illustrating the front and second of the information tag connector in a locked position.
Figure 2C:
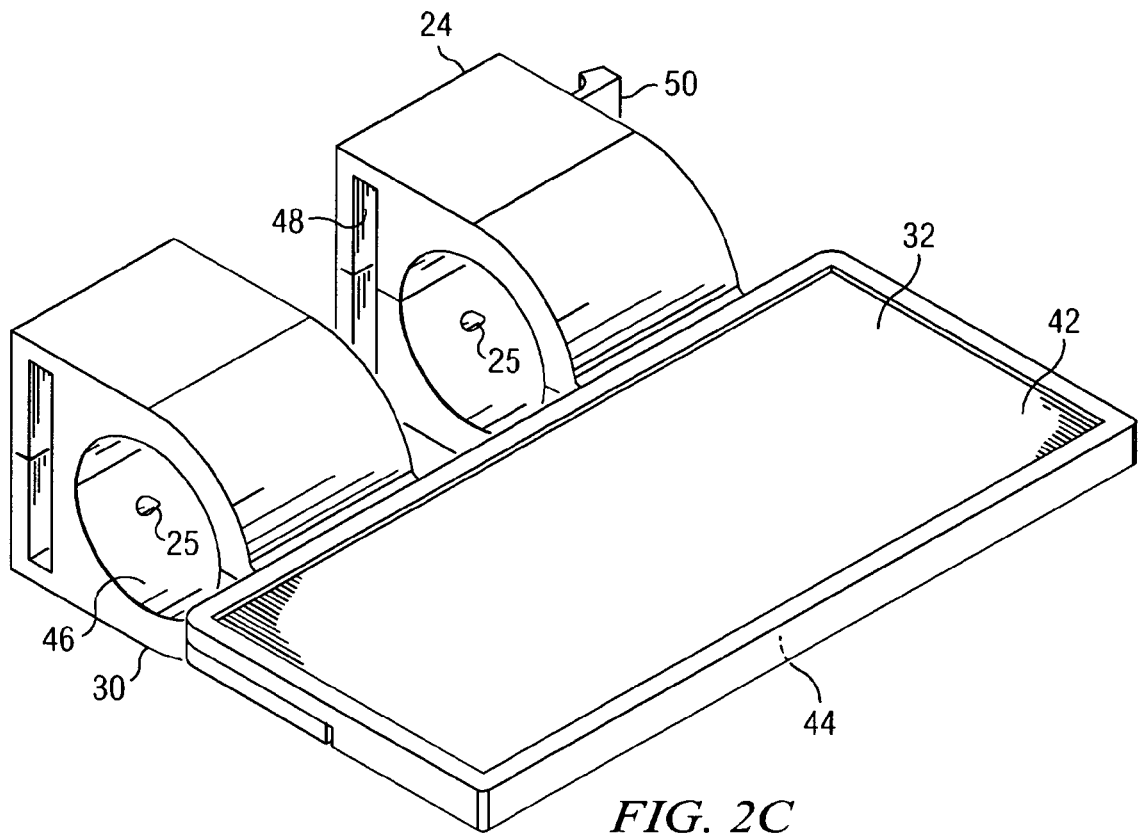
FIG. 2C is a perspective view illustrating the back and first of the information tag connector of FIG. 2A.

FIG. 2A is a perspective view of information tag connector 14 in an unlocked position. FIG. 2B is a perspective view illustrating information tag connector 14 in a locked position. FIG. 2C is a perspective view illustrating the back and first of information tag connector 14. Information tag connector 14 is adapted to removably couple with instrument 12. Information tag connector 14 is also adapted to removably couple with one or more accessories 17.

In an exemplary embodiment, connector 14 comprises a first portion, for example a top portion 18, and a second portion, for example a bottom portion 16, hingeably coupled to each other at a side 20 of connector 14. Bottom portion 16 and top portion 18 may be slide-and-snap fitted together to lock connector 14 over and around hose 15. Bottom portion 16 comprises a locking portion 22 coupled with one or more flanges 24. In the illustrated embodiment, the end of flange 24 distal from locking portion 22 is U-shaped. Although in the illustrated embodiment, two flanges 24 are shown, if desired, a fewer or greater number of flanges may be used. Flange 28 extends outwardly away from locking portion 22 such that an inner surface of flange 28 is substantially semi-circular in shape. Locking portion 22 comprises at least one locking hole 26.

Top portion 18 comprises an information tag portion 28 coupled to one or more flanges 30. Although in the illustrated embodiment, two flanges 30 are shown, if desired, a fewer or greater number of flanges may be used. Flange 30 extends outward away from information tag portion 28 in a direction opposite to that of the outward extension of flange 28. An inner surface of flange 30 is substantially semi-circular in shape. In the illustrated embodiment, the end of flange 30 distal from information tag portion 28 is U-shaped and oriented in an opposite direction to the orientation of the U-shaped end of flange 24 such that the openings of the U-shaped ends face each other. Flanges 24 and 30 are located along the length of connector 14 at corresponding portions of bottom portion 16 and top portion 18. Flanges 24 and 30 are hingeably coupled with each other at side 20. If desired, an inner surface of at least one of flange 24 or flange 30 may comprise one or more resistive elements 25, for example a protrusion, to prevent undesirable movement of connector 14 along hose 15 (FIG. 1A) of stethoscope 12. When information tag connector 14 is coupled to hose 15 with or without an accessory, the inner diameter of the slot formed by flanges 24 and 30 in combination with resistive elements 25 provides stability to information tag connector 14 and prevents slippage of connector 14 along hose 15 which may be of different diameters.

Information tag portion 28 (FIG. 2A) comprises of a message surface 32 and a name surface 34 opposite message surface 32. Name surface 34 has a cutaway portion 36 such that when connector 14 is in a locked position as illustrated in FIG. 2B, locking portion 22 rests in cutaway portion 36 such that a surface of non-cutaway portion 38 of name surface 34 and the surface of locking portion 22 are substantially flush with each other. Cutaway portion 36 comprises at least one locking hook 40 extending outwardly from the surface of cutaway portion 36 towards locking portion 22 of bottom portion 16 of connector 14. In the illustrated embodiment, the number of locking hooks 40 is equal to the number of locking holes 26. If desired, the number of locking hooks 40 may be more or less than the number of locking holes 26. An inner surface of locking hook 40 is curved and locking hook 40 is operable to engage with locking hole 26 in a slide-and-snap movement to configure connector 14 in a locked position. If desired, any mechanism for locking bottom portion 16 and top portion 18 of connector 14 may be used.

Message surface 32 may be used to display messages, for example, advertisements, company logos, slogans, trademarks or promotional messages. The messages may be from the pharmaceutical, medical or other industry. The message may be printed on a medium, for example paper, plastic, metal, and/or the like, and affixed (removably or irremovably) to message surface 32. If desired, a portion 42 of message surface 32 may be recessed so that when the medium is affixed to the recessed portion, the surface of the medium is substantially flush with the non-recessed portion of message surface 32, thereby making it difficult for the end user to remove the medium from message surface 32. If desired, the message may be pad printed, painted, or silk screened on message surface 32.

Non-cutaway portion 38 of name surface 34 may be used to display identifying information for the health care worker using instrument 12 (FIG. 1B). The identifying information may comprise the name, contact information, employee identification number, company name, and/or the like, of the health care worker. If desired, name surface 34 may be used to display messages. The identifying information may be printed on a medium, for example paper, plastic, metal and/or the like, and affixed (removably or irremovably) to non-cutaway portion 38. If desired, a portion 44 of non-cutaway portion 38 may be recessed so that when the medium is affixed to the recessed portion, the surface of the medium is substantially flush with the non-recessed portion of non-cutaway portion 38, thereby making it difficult for the end user to remove the medium from non-cutaway portion 38. If desired, the identifying information may be pad printed, painted, or silk screened on non-cutaway portion 38.

Figure 2D:
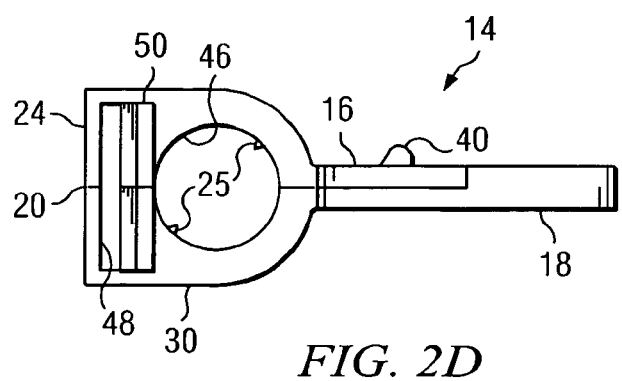
FIG. 2D is a front elevational view of the information tag connector of FIG. 2B.

FIG. 2D is a front elevational view of information tag connector 14 in a locked position. In the illustrated embodiment, in the locked position, the inner surface of flanges 24 and 30 form an instrument receiving slot 46 for receiving a portion of instrument 12, for example hose 15. Although in the illustrated embodiment, instrument receiving slot 46 is circular in shape, the invention is not so limited and slot 46 may be of any desired shape. For example, if information tag connector 14 is to be coupled to a square-shaped portion of an instrument, then instrument receiving slot 46 may be square in shape.

In the locked position, the U-shaped ends of flanges 24 and 30 cooperate to form an accessory receiving slot 48 for receiving a portion of an accessory, for example accessory 17 (FIG. 1A). Although in the illustrated embodiment, accessory receiving slot 48 is rectangular in shape, slot 48 may be of any desired shape. For example, if the portion of the accessory engaging with slot 48 is circular in shape, then accessory receiving slot 48 may be circular in shape.

Figure 3A:
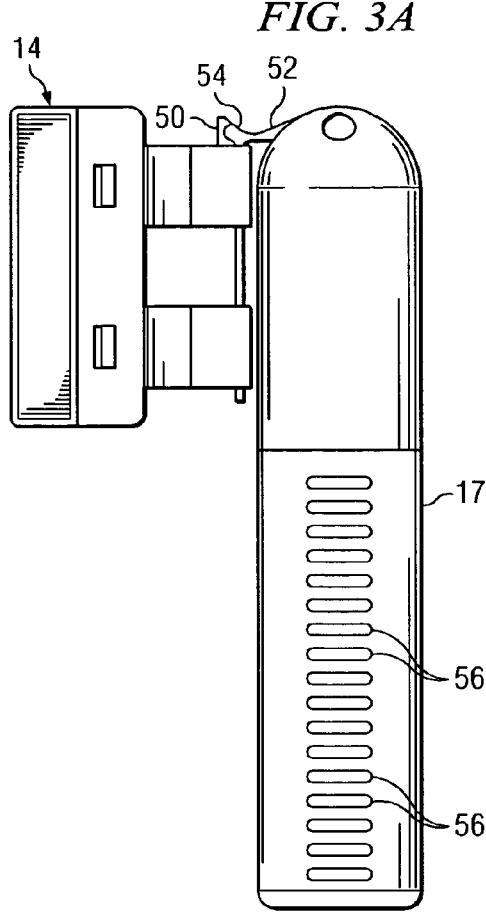
FIG. 3A is a top plan view illustrating an information tag connector coupled to an accessory.
Figure 3B:
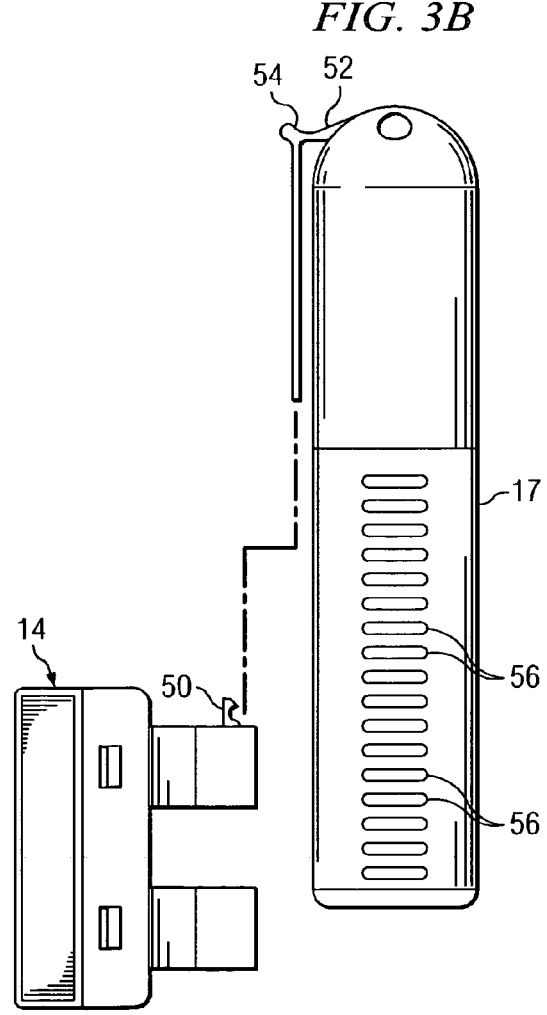
FIG. 3B is a top plan view illustrating an information tag connector with the accessory separated from the information tag connector.

FIG. 3A is a top plan view illustrating information tag connector 14 coupled to accessory 17 and FIG. 3B is another top plan view illustrating information tag connector 14 separated from accessory 17. Accessory 17 is adapted to removably couple with connector 14 on a side of connector 14 which is distal from information tag portion 28 of connector 14. Thus, when connector 14 is coupled to instrument 12 and accessory 17 is coupled to connector 14, the accessory and the information tag portion are on opposite sides of the instrument. An advantage of having the accessory and the information tag portions on opposite sides of the instrument is that the weight of either one is offset at least in part by the weight of the other one.

In the illustrated embodiment, a locking clip 52 is disposed on an outer surface of accessory 17. Locking clip 52 comprises a substantially L-shaped structure with the longer arm of the structure extending along the length of accessory 17. Locking clip 52 is operable to slide into accessory receiving slot 48 of connector 14 so that accessory 17 may be easily worn by the user of instrument 12. In an exemplary embodiment, in order to couple accessory 17 with connector 14, the longer arm of locking clip 52 is slid into accessory receiving slot 48. Locking clip 52 and/or accessory receiving slot 48 are shaped and/or sized such that the arm of locking clip 52 may be inserted into slot 48 without inadvertently disengaging from slot 48 due to movement of instrument 12, connector 14, and/or accessory 17.

Information tag connector 14 optionally comprises an accessory locking element 50. Accessory locking element 50 facilitates locking of accessory 17 in accessory receiving slot 48. In the illustrated embodiment, locking element 50 is disposed on or is part of flange 24 and/or flange 30. In an exemplary embodiment, locking element 50 comprises a locking hook extending outwardly from flanges 24 and 30 with a curved portion of the hook facing away from locking portion 22 of connector 14 substantially in the direction of accessory 17. Locking clip 52 of accessory 17 comprises a protrusion 54. When accessory 17 is coupled to connector 14, protrusion 54 engages with the curved portion of locking element 50 to prevent accessory 17 from inadvertently disengaging from connector 14. Although in the illustrated embodiment, locking clip 52 comprises protrusion 54, in an alternative embodiment, locking clip 52 may not comprise protrusion 54.

In the illustrated embodiment, the outside surface of accessory 17, which is in the form of a spray bottle, is provided with ribs 56 to facilitate better gripping of the accessory. The spray bottle is fitted with a simple atomizer, and is designed to be filled with a disinfectant, for example, an isopropanol solution (rubbing alcohol) or similar generally accepted germicidal agent used in stethoscope disinfection.

The cap of the spray bottle may be adapted so that the spray bottle may be worn in different ways, if desired. For example, the cap of the spray bottle may have a hole in proximity to the first to allow for a string attachment so that the spray bottle may be worn around the user's neck, if desired. Alternatively, the spray bottle may also be carried in a lab jacket or shirt pocket by itself using the locking clip. In this position, the outer surface of the locking clip could be used to display messages. The spray bottle may be used for regular disinfection of parts of the instrument, for example the head of the stethoscope, and its other parts, to help prevent cross-contamination between patients. After spraying, the user may simply wipe the stethoscope part with a clean, disposable tissue or similar dry cotton gauze or pad. The spray bottle may be used to disinfect medical instruments, devices or surfaces, for example, parts of the stethoscope, such as diaphragm, bell, hose, yoke, metal structure, and ear pieces; horoscope parts, ophthalmoscope parts, and the skin surface of a patient when performing a simple skin procedure.

A storage container may be provided as an accessory. In an exemplary embodiment, the storage container is shaped like a box and is adapted to removably couple with the tag. For example, the storage container may comprise a locking clip that slides into accessory receiving slot 48 of information tag connector 14 and may be easily worn by the user of the stethoscope. The locking clip of the storage container may be similar to locking clip 52 of FIG. 3B. The container may be used to carry simple medical supplies or other items in it, such as standard alcohol wipes to assist and encourage disinfection of the head and other components of the stethoscope or other medical instrument. The container may be used to store other objects, such as stethoscope parts, medicine vials, rings, keys, etc.

The information tag connector is adapted to couple with a stethoscope and an accessory, for example a spray bottle or a storage container, and is portable and wearable on the stethoscope hose and therefore highly accessible to the user. The information tag connector may be used as an informational, identification, promotional, or marketing tool. It encourages increased awareness of the dangers of contamination and subsequent possible vectorization of harmful viruses, bacteria, fungi, and other organic and inorganic contaminants by both the instrument and the health care worker in the health care setting. It provides an easy, convenient method for disinfection of the stethoscope to help reduce cross-contamination between patients, iatrogenic vectorization and nosocomial infections. As either accessory could be worn on the information tag connector, it provides convenient access to standard alcohol wipe pads and/or a disinfectant spray bottle for the health care worker, thereby providing high visibility of the disinfectant which acts as a reminder to encourage disinfection.

In accordance with an embodiment, the information tag connector is adapted to couple with a stethoscope and other accessories. These accessories when coupled to the information tag connector are highly visible and accessible to the user of the medical instrument. If desired, one or more of these accessories may be used as informational, identification, promotional or marketing tools and may also be used for medically relevant purposes. For example, a watch may be used to assist with the measurement of a patient's pulse; a calculator may be used to assist with the calculation of patient drug doses, for example in pediatrics, the intensive care unit, etc.

Although in the exemplary embodiment, the accessory receiving slot is part of the information tag connector and the locking clip is part of the accessory, if desired, the locking clip may be part of the information tag connector and the slot may be part of the accessory. Furthermore, any mechanism for removably coupling the accessory to the information tag connector may be used. If desired, in an alternative embodiment, the information tag connector may also comprise a component similar to the cap of the spray bottle and the accessories may be removably coupled to the component.

The information tag connector and/or the accessories may be made of simple plastic polymers, such as polypropylene, polyethylene, rubber, metal, and/or any other material or combination thereof. Other materials may be used if desired. If desired, the information tag connector, the accessories, and/or parts thereof may be made with an added polymer of triclosan, or other similar antimicrobial agent, to give the connector and/or the accessory built in antimicrobial properties.

The information tag connector, the accessories and/or any of their parts, for example the spray bottle, calculator, watch, storage container, the writing instrument, the portable light source, the ruler instrument, and/or the voice recorder, may be used for advertisement, for example by displaying company logos, slogans, trademarks or promotional messages. If desired, the information tag connector, the accessories and/ or any of their parts may be used as a promotional product in the pharmaceutical or any other medical or non-medical industry.

Although orientation specifying terms, such as top, bottom, front and back, are used herein to describe an exemplary embodiment of the present invention, it should be understood that such terms are used only to describe the relative position of various parts in an exemplary embodiment, and that the information tag connector, the instrument and/or the accessory may be oriented in any direction.

What is claimed is:

1. The integrated name tag and accessory holder for a medical instrument, the integrated name tag and accessory holder comprising:
    a central connector adapted for connecting to an elongated portion of a medical instrument;
    a name tag attached to, and extending from, the central connector, the name tag having a first surface for receiving a printed message;
    an accessory holder attached to the connector on a side opposite of the name tag, the accessory holder and name tag thereby disposed on opposite sides of the central connector;
    an accessory including a clip;
    wherein the name tag is comprised of a first surface for displaying graphical elements and the accessory holder is comprised of an opening for receiving a portion of an accessory;
    wherein the accessory holder receives the clip attached to the accessory; and
    wherein the accessory includes a disinfectant spray bottle.

2. An integrated name tag and accessory holder for a medical instrument, the integrated name tag and accessory holder comprising:
    a central connector adapted for connecting to an elongated portion of a medical instrument;
    an name tag attached to, and extending from, the central connector, the name tag have a first surface for receiving a printed message; and
    an accessory holder attached to the connector on a side opposite of the name tag, the accessory holder and name tag thereby disposed on opposite sides of the central connector;
    an accessory wherein the name tag is comprised of a first surface for displaying graphical elements and the accessory holder is comprised of an opening for receiving a portion of an accessory;
    wherein the connector is comprised of a hinged clamp.

3. An integrated name tag and accessory holder for a medical instrument, the integrated name tag and accessory holder comprising:
    a central connector adapted for connecting to an elongated portion of a medical instrument;
    an name tag attached to, and extending from, the central connector, the name tag have a first surface for receiving a printed message; and
    an accessory holder attached to the connector on a side opposite of the name tag, the accessory holder and name tag thereby disposed on opposite sides of the central connector;
    an accessory wherein the name tag is comprised of a first surface for displaying graphical elements and the accessory holder is comprised of an opening for receiving a portion of an accessory;
    wherein the name tag, accessory holder and connector are integrally formed of a single, molded element having a portion folded over onto itself to cooperate and form the opening and the connector.

4. The integrated name tag and accessory holder of claim 3, wherein the single, molded element includes hooks for removably securing the folded-over portion to the single, molded element.

5. An integrated name tag and accessory holder for a medical instrument, the integrated name tag and accessory holder comprising:
    a central connector adapted for connecting to an elongated portion of a medical instrument;
    an name tag attached to, and extending from, the central connector, the name tag have a first surface for receiving a printed message; and
    an accessory holder attached to the connector on a side opposite of the name tag, the accessory holder and name tag thereby disposed on opposite sides of the central connector;
    an accessory wherein the name tag is comprised of a first surface for displaying graphical elements and the accessory holder is comprised of an opening for receiving a portion of an accessory;
    wherein the accessory is selected from the group consisting of a spray bottle, a calculator, a watch, a storage container, and a writing instrument.

6. An integrated name tag and accessory holder for a medical instrument, the integrated name tag and accessory holder comprising:
    a central connector adapted for connecting to an elongated portion of a medical instrument;
    an name tag attached to, and extending from, the central connector, the name tag have a first surface for receiving a printed message; and
    an accessory holder attached to the connector on a side opposite of the name tag, the accessory holder and name tag thereby disposed on opposite sides of the central connector;
    an accessory wherein the name tag is comprised of a first surface for displaying graphical elements and the accessory holder is comprised of an opening for receiving a portion of an accessory;
    wherein the name tag further includes a second surface opposite the first surface for receiving a printed message.

* * * * *